United States Patent
Hilbig et al.

(10) Patent No.: US 8,821,828 B2
(45) Date of Patent: Sep. 2, 2014

(54) METHOD FOR GENERATING NITRIC OXIDE

(75) Inventors: Rainer Hilbig, Aachen (DE); Robert Pinter, Lubeck (DE); Claudia Hannelore Igney, Aachen (DE)

(73) Assignee: Koninklijke Philips N.V., Eindhoven (NL)

( * ) Notice: Subject to any disclaimer, the term of this patent is extended or adjusted under 35 U.S.C. 154(b) by 143 days.

(21) Appl. No.: 13/517,057

(22) PCT Filed: Dec. 16, 2010

(86) PCT No.: PCT/IB2010/055856
§ 371 (c)(1),
(2), (4) Date: Jun. 19, 2012

(87) PCT Pub. No.: WO2011/077327
PCT Pub. Date: Jun. 30, 2011

(65) Prior Publication Data
US 2012/0258034 A1  Oct. 11, 2012

(30) Foreign Application Priority Data

Dec. 23, 2009 (EP) ..................................... 09180521
Apr. 23, 2010 (EP) ..................................... 10160906

(51) Int. Cl.
*C01B 21/30* (2006.01)

(52) U.S. Cl.
CPC ..................................... *C01B 21/30* (2013.01)
USPC ........................................................ 423/405

(58) Field of Classification Search
CPC ..... A61M 11/00; A61M 15/00; A61M 15/02; A62B 7/10; C01B 21/04; C01B 21/0438; C01B 21/045; C01B 21/0477; C01B 21/24; C01B 21/28; C01B 21/30; C01B 21/32; A61K 33/00

USPC ......... 423/385, 405, 406; 424/718; 95/43, 45, 95/47, 54, 90, 128, 130
See application file for complete search history.

(56) References Cited

U.S. PATENT DOCUMENTS 2,422,081 A  6/1947  Cottrell
2,643,937 A  6/1953  Pike
(Continued)

FOREIGN PATENT DOCUMENTS

GB  191018475  8/1910
WO  WO9317741  9/1993

OTHER PUBLICATIONS

K. Vonbank et al., Controlled prospective Randomised Trial on the Effects on Pulmonary Haemodynamics of the Ambulatory long Term Use of Nitric oxide and Oxygen in Patients with Severe COPD, Thorax 2003; 58:289-293.

*Primary Examiner* — Anthony J Zimmer
*Assistant Examiner* — Justin Bova
(74) *Attorney, Agent, or Firm* — Michael W. Haas

(57) ABSTRACT

The invention relates to a method for generating nitric oxide, in particular for therapeutic applications, which comprises the steps of: guiding a process gas into a reaction chamber 3, wherein the process gas comprises nitrogen and oxygen, heating the process gas to a temperature which is sufficiently high to enable a reaction of oxygen and nitrogen to form nitric oxide, thereby forming a gas which comprises nitric oxide, and extracting the nitric oxide comprising gas from the reaction chamber 3, wherein oxygen is present in the process gas in the reaction chamber in an amount of <5 vol-%.

13 Claims, 4 Drawing Sheets

(56) References Cited

U.S. PATENT DOCUMENTS

| | | |
|---|---|---|
| 6,296,827 B1 | 10/2001 | Castor et al. |
| 6,955,790 B2 * | 10/2005 | Castor et al. ............. 422/186.04 |
| 7,100,543 B2 | 9/2006 | Davidson |
| 2001/0031230 A1 | 10/2001 | Castor et al. |
| 2003/0064028 A1 | 4/2003 | Fine et al. |

* cited by examiner

METHOD FOR GENERATING NITRIC OXIDE

FIELD OF THE INVENTION

The invention relates to the field of nitric oxide generation. More particularly, the invention relates to mobile nitric oxide generation for home care applications.

BACKGROUND OF THE INVENTION

It is widely known to use nitric oxide in a variety of applications, for example as intermediate in the Ostwald process for the synthesis of nitric acid from ammonia. Additionally, several therapeutic applications are known.

As an example, nitric oxide is used by the endothelium of blood vessels to signal the surrounding smooth muscle to relax, thus resulting in widening the blood vessels and therefore increasing blood flow. This leads to nitric oxide being particularly applicable for blood pressure disease. However, many comparable or other applications are known for the use of nitric oxide. Exemplary applications for nitric oxide are for improving lung function and for treating or preventing bronchoconstriction or reversible pulmonary vasoconstriction, etc, for treating or preventing arterial restenosis resulting from excessive intimal hyperplasia in mammal, for Treatment of infected tissue e.g. to kill bacteria involving topical delivery of a source of nitric oxide containing gas to a skin surface containing infected tissue. One of the most famous applications of nitric oxide, however, is the administration for patients having the Persistent Pulmonary Hypertension (PPHN).

Nitric oxide may be administered in several ways. It is known to provide nitric oxide containing gases in gas cylinders. However, the handling and storage of the latter is complex with respect to safety measures. Furthermore, with respect to therapeutic applications, the stored gases have to comply with highly demanding requirements. It is thus much more advantageous to use an on-demand administration. This enables nitric oxide being generated directly before use and thus avoiding the safety and storage problems. Such an on-demand administration is very well suitable especially for home care applications. For enabling home care applications of nitric oxide, a mobile generation of nitric oxide is most favorable.

Methods are known to generate nitric oxide, including mobile nitric oxide generation. For example, it is known to generate nitric oxide by an electric gas discharge using only air and a source of electricity. This state of the art may be used exemplarily in medical or urgent care facilities for delivering a therapeutically-effective concentration of nitric oxide mixed with other gases to a specific organ of a human body.

The major drawback of the methods known from the state of the art is the considerable formation of nitrogen oxides in higher oxidized states. As an example, nitrogen dioxide is formed. Due to the high toxicity of these nitrogen oxides in higher oxidation states, especially nitrogen dioxide, the generated gas mixture cannot be used directly, but further purification steps are required instead.

SUMMARY OF THE INVENTION

It is an object of the invention to provide a method for generating nitric oxide which overcomes the limitations as set forth above.

It is a further object of the invention to provide a method for generating nitric oxide in which the formation of nitrogen oxides in higher oxidation states, especially nitrogen dioxide, is effectively prevented.

It is a further object of the invention to provide a method for generating nitric oxide which is easy to perform and which may be used in home care applications.

At least one of these objects is achieved by a method for generating nitric oxide, in particular for therapeutic applications, which comprises the steps of: guiding a process gas into a reaction chamber, wherein the process gas comprises nitrogen and oxygen, heating the process gas to a temperature which is sufficiently high to enable a reaction of oxygen and nitrogen to form nitric oxide, thereby forming a gas which comprises nitric oxide, and extracting the nitric oxide comprising gas from the reaction chamber, wherein oxygen is present in the process gas in the reaction chamber in an amount of ≤5 vol-%.

It is thus an essential feature of the present invention to use a low oxygen content of the process gas in the reaction chamber. It is thus possible to either use a process gas with the desired oxygen content. It is furthermore possible to use a process gas with a higher oxygen content, thereby reducing the oxygen content before the process gas enters the reaction chamber. This leads to the advantage that only a very small amount of oxygen is left in the reaction volume which may further oxidize a component into a nitrogen oxide with a higher oxidation state. As an example, it is well known that nitric oxide tents to be oxidized to nitrogen dioxide. Nitrogen dioxide, however, is a very toxic gas which must be removed by purification steps before application.

According to the invention, the formation of nitrogen oxides in higher oxidation states and thus the formation of toxic side products is substantially prevented. The generated nitric oxide containing gas may therefore directly be used for therapeutic applications, or medical applications, respectively. A direct administration of patients is thus possible. Complex or expensive purification steps are not necessary as nitric oxide is present in a pure or substantially pure nitrogen atmosphere at nearly atmospheric density.

Furthermore, even by using such a small amount of oxygen in the process gas in the reaction chamber in a manner like stated above, a therapeutically-effective concentration of nitric oxide may be provided. Thus, no concentrations steps are necessary, but the generated gas may be used for a direct administration on-demand.

The nitric oxide containing gas is preferably a gas mixture comprising nitrogen, and nitric oxide. However, nitrogen is present in a big excess thus playing the role of an inert gas. In case some oxygen is still present in the generated gas mixture and will react with the nitric oxide, the formation of nitrogen dioxide is in any case under a harmful level and has thus no negative effect.

Furthermore, the method according to the invention provides good system maintenance possibilities because there is no consumption and poisoning of chemical compounds due to chemical reactions.

The apparatus which has to be used for a method according to the invention may be simple, light weight and energy efficient.

In a preferred embodiment of the present invention, oxygen is present in the process gas in the reaction chamber in such an amount, that the comprised oxygen is completely or at least substantially completely converted into nitric oxide. This means that the process gas is treated to only comprise a strongly reduced oxygen content in the reaction chamber. Then, all, or nearly all of the comprised oxygen reacts to nitric oxide in the reaction chamber. Only an insignificant amount of oxygen may be present in the generated gas mixture after the reaction.

In a further preferred embodiment of the invention, air is used as process gas. This is especially advantageous for home care applications. Furthermore, no process gases have to be stored. This embodiment of the method according to the invention is simple to perform and cost-saving.

In a further preferred embodiment of the present invention, oxygen is present in the process gas in the reaction chamber with a partial pressure of 20 Pa. This is a concentration in which the formation of nitrogen oxide in higher oxidation states is nearly completely prevented, whereas the generated nitric oxide comprising gas is concentrated enough for being therapeutically effective.

In a further preferred embodiment, nitric oxide is present in the generated nitric oxide containing gas in an amount of $\geq 10$ ppm-$\leq 1000$ ppm. This is an amount which may easily be reached even with an oxygen content in the process gas being reduced such as set forth above. Furthermore, this concentration of nitric oxide in the generated gas is sufficiently high to reach a therapeutically-effective level. The gas may thus be used directly for administration.

In a further preferred embodiment of the present invention, the process gas is heated to a temperature range of $\geq 1000K$. This temperature range enables an effective reaction of oxygen and nitrogen, thereby being energy saving.

In a further preferred embodiment of the present invention, the reaction chamber is isolated by a heat isolation. This measure further reduces the energy input and thus improves the energy efficiency for effectively heating the reaction chamber and thus the process gas. Thus, this embodiment is especially cost-saving.

In a further preferred embodiment of the present invention, the oxygen content in the reaction chamber is achieved by guiding the process gas through a first membrane. This is a very effective measure to form a process gas with a sufficiently low oxygen content even when starting with a process gas having a greater amount of oxygen. The suitable membranes have a long lifetime and only low requirements with respect to maintenance. Furthermore, by providing a first membrane for reducing the oxygen content, the method according to the invention may be carried out very easily on-demand, i.e. directly before use. No special process gases have to be stored.

In a further preferred embodiment of the present invention, the generated nitric oxide comprising gas is extracted from the reaction chamber into an extraction chamber through a second membrane. This is a special simple and cost-saving way to extract the generated gas and provide the latter for administration.

In a further preferred embodiment of the present invention, a swing process is used. The swing process is a process, in which a heating phase of the reaction chamber is followed by a cooling phase. This enables the membranes to be regenerated and thus optimal reaction conditions. In this case, it is especially preferable, if two reaction chambers are used in a parallel arrangement. According to this, a continuous flow of generated nitric oxide containing gas may be generated, especially when working in an opposing phase.

In a further preferred embodiment of the present invention, the method comprises the following additional steps:
providing a first chamber, the first chamber comprising an additional gas, the
additional gas comprising nitrogen;
obtaining nitrogen gas from the additional gas;
using obtained nitrogen gas as a carrier gas for transporting nitric oxide extracted from the reaction chamber and/or guiding obtained nitrogen gas into the reaction chamber.

This embodiment has the advantage that it enables transport of nitric oxide extracted from the reaction chamber to a location where the nitric oxide is needed by using obtained nitrogen gas as a carrier gas. Another or additional advantage is that the obtained nitrogen gas can be used to generate the process gas.

In a further preferred embodiment of the present invention, the method comprises the following additional steps:
providing the additional gas such that it comprises nitrogen and oxygen;
obtaining oxygen gas from the additional gas;
guiding at least part of the obtained oxygen gas into the reaction chamber.

This embodiment has the advantage that the obtained oxygen gas can be used to generate the process gas. Another part of the obtained oxygen gas may be used for other purposes such as administering it to a patient. Such other purposes may be pursued in addition to or instead of using obtained oxygen gas to generate the process gas.

BRIEF DESCRIPTION OF THE DRAWINGS

These and other aspects of the invention will be apparent from and elucidated with reference to the embodiments described hereinafter.

In the drawings.

DETAILED DESCRIPTION OF EMBODIMENTS

Figure 1:
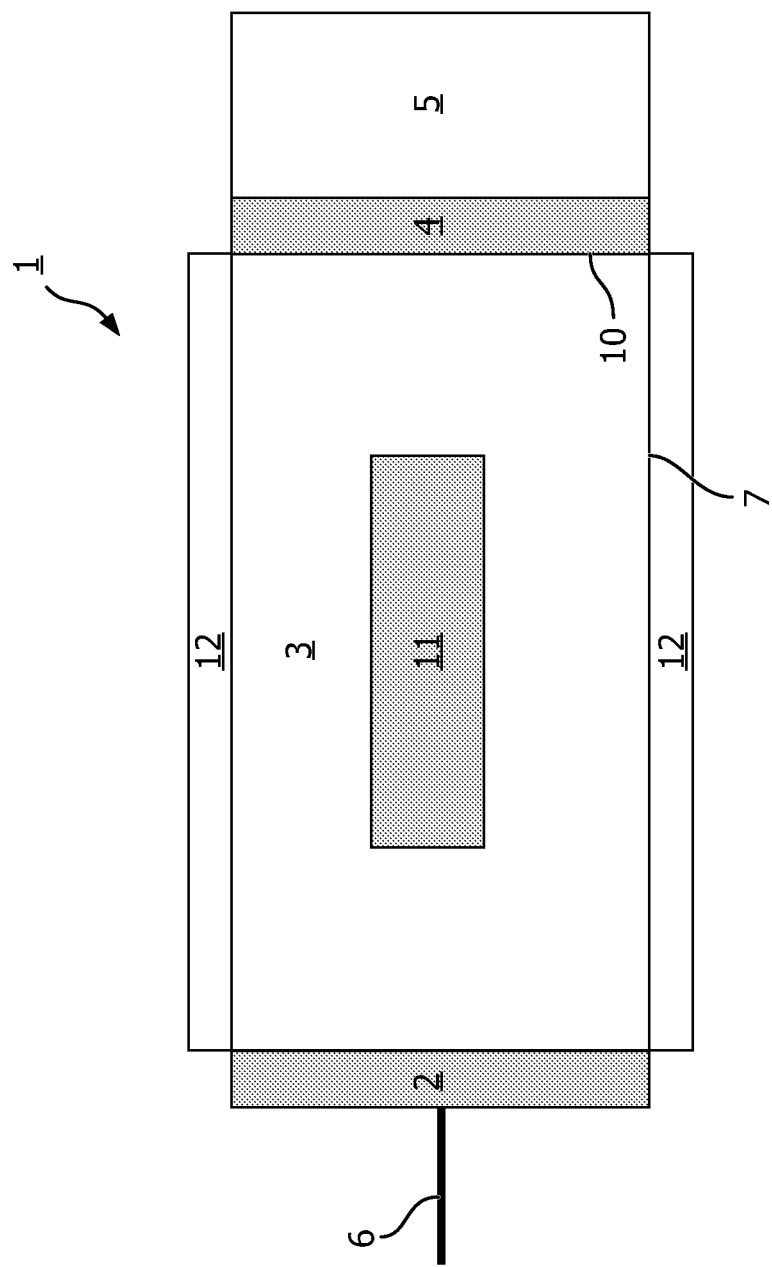
FIG. 1 shows a schematical view of an arrangement designed for a method according to the invention.

In FIG. 1, an arrangement 1 is schematically shown. The arrangement 1 may comprise a first membrane 2 to prepare a process gas, a reaction chamber 3 for carrying out the reaction of nitrogen and oxygen, a second membrane 4 for purifying the generated gas, and an extraction chamber 5 for extraction of the generated nitric oxide containing gas. The arrangement 1 is designed for carrying out a method for generating nitric oxide according to the invention, as will be apparent below.

According to the invention, a gas which at least partly comprises nitric oxide is generated. Therefore, a process gas as base material is used. The process gas may be any kind of gas which at least partially comprises nitrogen and oxygen, which are the educts for the formation of nitric oxide. However, it is preferred, that the process gas substantially consists of nitrogen and oxygen, wherein an excess of nitrogen is advantageous. It may thus be preferred to use air as process gas. The reaction chamber 3 may therefore be connected to a gas inlet 6 which is equipped with a pump, which forces the process gas, for example air, through the gas inlet 6 into the reaction chamber 3.

According to the invention, it is essential to use a process gas with a low oxygen content, i.e. with an oxygen content which lies in the range of $\leq 5\%$ by volume (vol-%) in the reaction chamber. The use of a reduced oxygen content in a nitrogen surrounding is a well suited measure to suppress the higher oxidized states of NO ($NO_x$). Especially, the very toxic nitrogen dioxide may be hold below harmful levels. The amount needed for medical applications can be delivered also with reduced oxygen content. It may be noted that besides reducing the oxygen content in the process gas when starting with a higher oxygen content, a decrease of the total pressure may be advantageous. Such a decrease in pressure is also a reduction of the absolute amount of oxygen present and may be used in combination with a further reduction of oxygen pressure in the process gas. It has to be noted that a corresponding effect (suppressing higher oxidation states of nitrogen oxides) may be realized by using elevated temperatures. Consequently, a combination of both reducing the oxygen content and elevating the temperatures may be advantageous.

However, to achieve an application of a process gas with a reduced oxygen content in the reaction chamber, the process gas is guided through the gas inlet 6 into the reaction chamber 3, thereby passing the first membrane 2. The first membrane 2 has as objective to reduce the oxygen content in the process gas to an amount of ≤5 vol-%, or, in a preferred embodiment, to an amount in which all the oxygen which is still present in the reaction chamber 3, may react to nitric oxide. Exemplary oxygen contents may be in the range of a partial pressure of 20 Pa.

A simple way to form this first membrane 2 is to use a membrane that better permeates nitrogen than oxygen. This membrane may be dense with respect to oxygen. This means that the membrane is permeable for most gases, especially for nitrogen, whereas it has very decreased permeation properties with respect to oxygen. In this case, membrane 2 may be designed as a plug in the gas inlet 6. It is furthermore possible to design membrane 2 as a closure for the reaction chamber 3. However, it is important, that the process gas is guided through the first membrane 2 before entering the reaction chamber 3.

Instead of using permeation properties of the membrane 2 with respect to reducing the oxygen content, the first membrane 2 may also be designed to decrease the oxygen content by adsorption of oxygen. In this case, the first membrane 2 may be positioned like stated above, or, alternatively, in the reaction chamber 3 as such. In this case, the process gas may be directly guided to the reaction chamber 3 instead of applying it via the first membrane 2.

Furthermore, the decrease of oxygen content in the process gas being present in the reaction chamber 3 may be realized by a nitrogen separator. This nitrogen separator (like that of UBE Industries) may comprise a polyimide membrane module, which mainly consists of hollow-fiber membranes. The permeation of oxygen towards the outer side is enabled, leading to the remaining nitrogen having a very low oxygen content. As an exemplary value, the so generated process gas may have a nitrogen purity of 99%. A corresponding effect may be reached by using zeolithes. In this case, oxygen is permeated through the outside, whereas the retentate flow has a strongly reduced oxygen content.

Another possibility is the usage of reversibly oxygen-fixating agents, i.e. an oxygen selective material, such that the oxygen of the process gas is adsorbed by said agent.

However, it has to be noted that the first membrane 2 may be omitted if the process gas is generated by mixing basic gases, especially oxygen and nitrogen in such a way, that the amount of oxygen lies in the described range. Hereto, defined amounts of nitrogen and oxygen may be guided into the reaction chamber 3. This may be performed by inserting both a defined amount of nitrogen and oxygen through two gas inserts. It is furthermore possible to mix pure nitrogen and oxygen directly before inserting them into the reaction chamber 3. However, it is preferred to reduce the oxygen content directly before use by a first membrane 2 because in this case, no basic gases have to be stored which is especially advantageous for home care applications.

The concentration of oxygen may further be decreased by using inert gases or rare gases, respectively as carrier. Possible carriers may be nitrogen, or argon.

Downstream the first membrane 2, the process gas having a reduced oxygen content is guided into the reaction chamber 3 to carry out the reaction of oxygen and nitrogen to form nitric oxide.

The reaction chamber 3 is at least partly surrounded by a wall 7. The wall 7, and thus the reaction chamber 3 may be of any suitable configuration; however a tubular shape may be preferred. Materials of interest for forming the wall 7 are plastics, glass, ceramics etc. The reaction chamber 3 may be closed on two opposite sides by the first and second membrane 2, 4, respectively, like it is shown in FIG. 1. However, it may be advantageous that the membranes 2, 4 are only small plugs inside the gas inlet 6 or a gas outlet 8, respectively. In the latter case, the membranes 2, 4 are at least partly replaced by end walls formed by the wall material 7 and form, as such, part of the wall 7.

To enable the reaction of the process gas, the process gas has to be heated to an elevated temperature. The heating of the process gas with reduced oxygen content is very quick leading to the possibility of an nitric oxide supply on-demand, This further reduces the danger of the nitric oxide being oxidized and to form nitrogen oxides in higher oxidation states.

To heat the process gas, a heating device 11 is provided. The heating device 11 may be any suitable heating device which is designed to heat the process gas. The heating device 11 is preferably connected to an electrical power source being located outside the reaction chamber 3. The electrical connection between the heating device 11 and the power source may be just wires, which preferably are arranged to electronically connect the heating device 11 in the reaction chamber 3 to the outside electrical power source.

One suitable heating device 11 comprises electrodes and is designed for gas discharge burning, thereby generating a plasma, wherein the process gas is in contact with the plasma formed by the gas discharge. In this case, very high temperatures may be used, for example, temperatures of more than 3300 K may be suitable. In this case, it is important to use an electrode material which is inert at the present conditions. It may furthermore be possible to use an electric discharge, which is based on capacitive, inductive or microwave coupling and thus electrode-less. In this case, material loss of discharge electrodes can be avoided. The application of a plasma is furthermore advantageous, because a plasma comes up with the additional advantage of emitted blue and UV-light. The amount of nitrogen dioxide present in the reaction chamber 3 is thereby further reduced due to a photo-dissociation steep of nitrogen dioxide to nitric oxide.

Another possible heating device 11 is a device which may directly be heated by electrical current and which is based on a conductive material. For example, this may be a metallic filament or semiconductor material. Exemplary materials may be filaments from platinum, tantalum and osmium, a Nernst-glower (rare earth oxides) or siliciumcarbide. However, it is important that the used materials are inert against the conditions in the reaction chamber 3. In this case, temperatures of about 1000K or more (≥1000K) may be sufficient.

It is furthermore possible to use indirectly heated isolating materials. Simple examples may be quartz glass tubes and aluminum oxide tubes (DGA), e.g. heated by a tungsten wire (e.g. a halogen incandescent lamp) or heated by a gas discharge (high intensity discharge lamps in quartz or DGA). Again, the used materials have to be sufficiently inert and temperatures of about 1000K or more (≥1000K) may be sufficient.

Another possible heating device 11 is designed to heat the process gas from the outside (externally heating). This may be enabled by applying an externally applied field (i.e. microwave, laser, light, etc.).

However, any heating device 11 may be used which enables the process gas to be heated to a temperature range allowing the nitrogen and the oxygen to react. It has to be noted that elevated temperatures Twall>600K might be applied to the wall independent from the way of heating the process gas to suppress further oxidation. That means that the formation of nitrogen dioxide from nitric oxide with eventually remaining oxygen is further prevented.

To realize an effective and energy efficient heating of the process gas, a heat isolation 12 may be provided. The heat isolation 12 may be arranged outside the wall 7 or inside the reaction chamber 3, preferably connected to the wall 7. It decreases the amount of energy which is necessary to heat the process gas to an amount which is sufficiently high to allow a reaction of nitrogen and oxygen to form nitric oxide. This heat isolation 12 may be designed to work against losses by heat conductivity and/or by heat radiation. Well known measures are, for example, applying a vacuum (conductivity) or applying e.g. metallic reflecting layers (radiation). The wall 7 itself can also be used for heat isolation by making it from metal, for example, or from any isolating material known as such.

With respect to the reaction of nitrogen and oxygen to form nitric oxide, a swing process might be advantageous. During a heating phase, nitric oxide is generated and directly forced to flow into the extraction chamber 5 due to a total pressure or partial pressure gradient induced by the temperature increase of the gas in the reaction chamber 3. During this phase, the first membrane 2 may also release adsorbed oxygen towards, for example, the air, and thus back through the gas inlet 6. During a cooling phase, the flow rate into the reaction chamber 3 of oxygen and, depending on the kind of embodiment, nitrogen is increased due to a total pressure or partial pressure gradient between e.g. air and the reaction chamber 3 due to a temperature decrease of the gas in the reaction chamber 3. However, a continuous generation of nitric oxide is possible by providing, for example, two reaction chambers 3 working in an opposing phase.

The amount of nitric oxide being delivered per second can be adapted to the demand of the application by gas temperature adaption and/or by pulsed power deposition (on-off switching periods, for example).

Downstream the reaction chamber 3, the second membrane 4 may be provided. This second membrane 4 is a membrane being permeable for nitric oxide. It is used to further purify the nitric oxide that is extracted from the reaction chamber 3 into the extraction chamber 5. It is thus apparent that the second membrane 4 may be omitted by providing a gas mixture in the reaction chamber 3 after the reaction, which is suitable for direct use. This may be realized by providing the respective process gas. In this case, the second membrane may be exchanged by a valve.

However if a second membrane 4 is used, its permeability for nitrogen oxides of higher oxidation states ($NO_x$) and furthermore for oxygen to prevent a later oxidation of nitric oxide by the oxygen is strongly reduced. The second membrane 4 may also be used as a part of the wall 7. In this case, it is preferred to use membranes that are non-permeable for nitric oxide, but are highly permeable for higher oxidized states of nitric oxides. For such membranes for example polydimethyl siloxane (PDMS) as supplied by PermSelect can be used. In this case, the second membrane 4 is not used as a separation of the reaction chamber 3 and the extraction chamber 5, but as a part of the wall 7. Then, the unwished higher oxidized nitrogen oxides are guided, for example, to the atmosphere, where they may be collected, whereas the nitric oxide containing gas is guided through the gas outlet 10.

Referring to the extraction chamber 5, the latter has as objective to extract the generated nitric oxide from the reaction chamber 3. This enables the generated nitric oxide being applicable for the medical applications, i.e. the administration for a patient as inhalation gas or the like. By providing a second membrane 4 as separation between the reaction chamber 3 and the extraction chamber 5, nitric oxide may be extracted by a flow of the process gas, or the generated nitric oxide containing gas, respectively.

The extraction chamber 5 may as well be designed as the lower pressure side of a compressor system, in an extreme case of a vacuum pump, which compresses nitric oxide enriched gas in this chamber to come back to standard pressure conditions. The main extracted component will be nitrogen, which also (partly) permeates through the second membrane.

In case that the second membrane 4 is omitted, i.e. the extraction chamber 5 is in direct contact with the reaction chamber 3, the extraction chamber 5 is equipped with a valve, that opens or closes the apparatus against the area to apply nitric oxide depending on status of operation.

Figure 2:
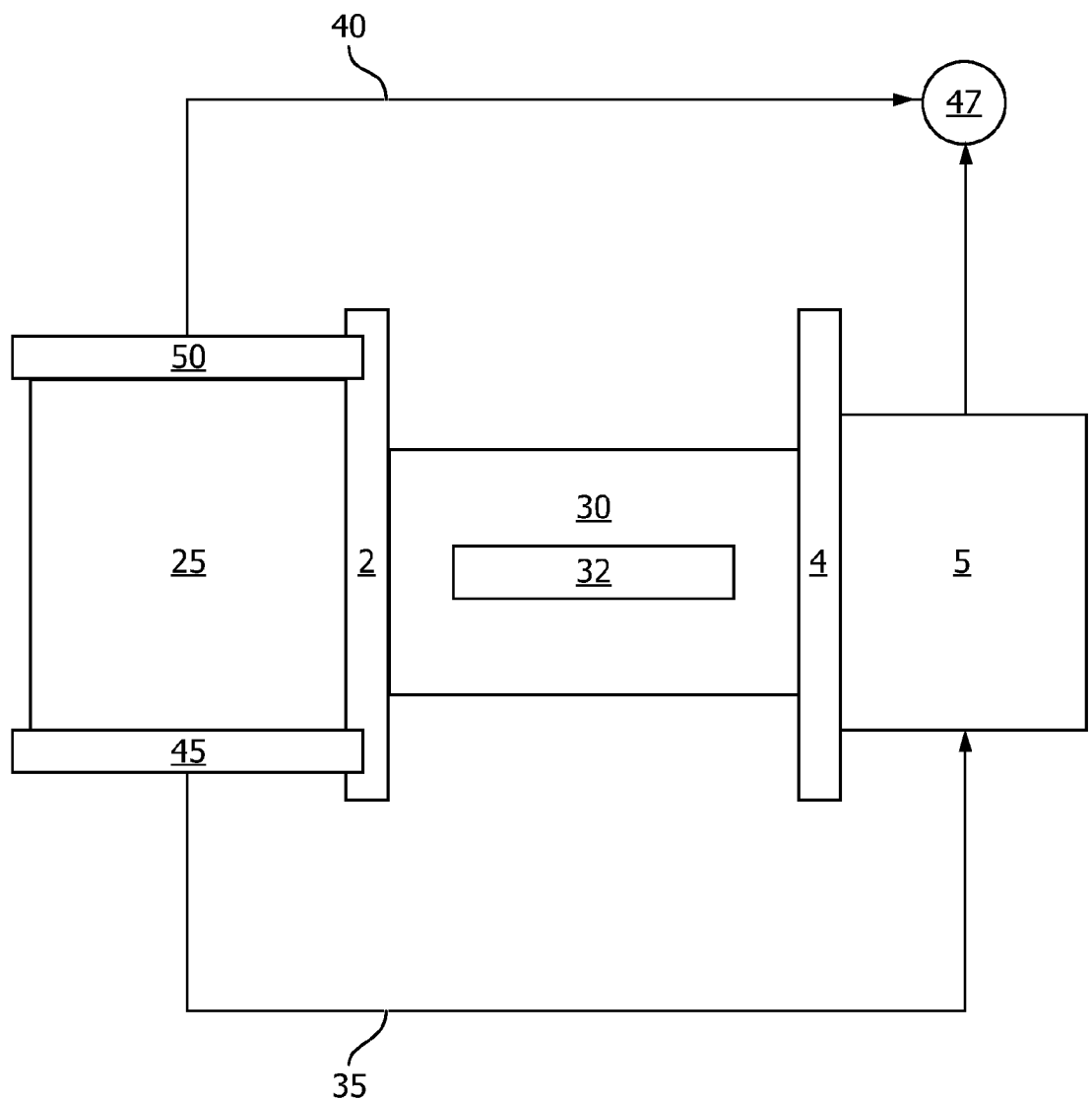
FIGS. 2-3 show additional schematical views of arrangements designed for a method according to the invention.
Figure 3:
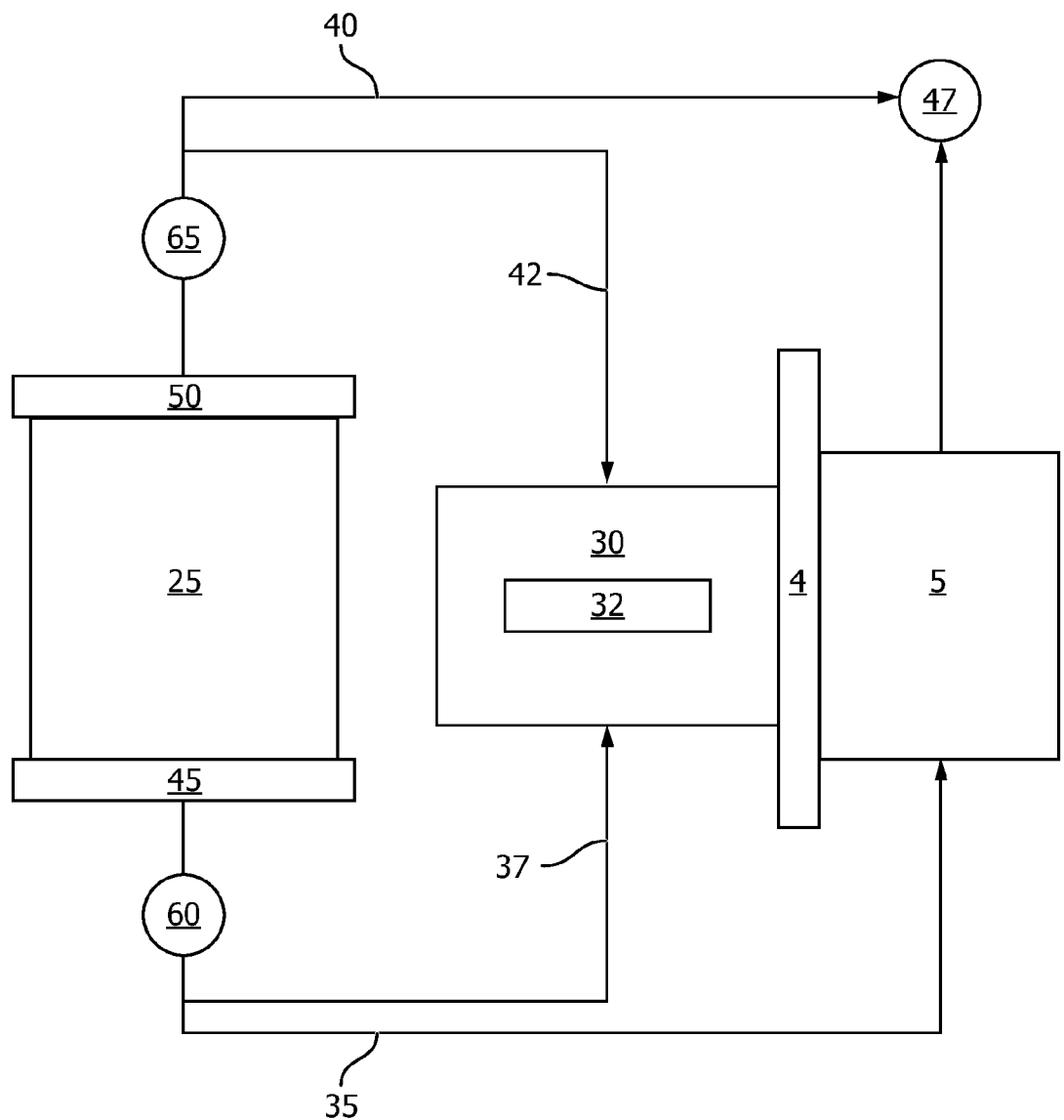
Figure 4:
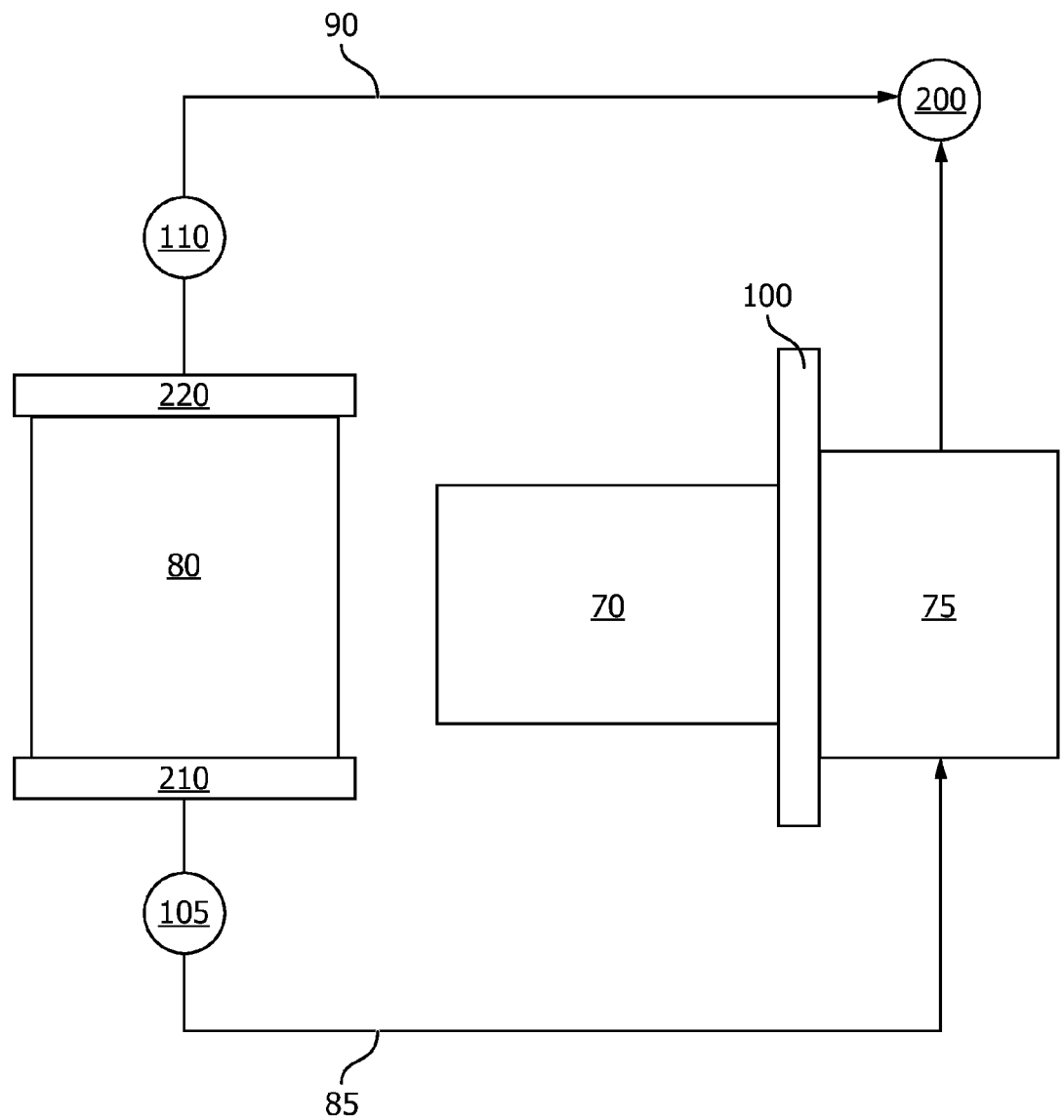
FIG. 4 schematically shows a generalization of the concept behind the present invention.

FIGS. 2-4 show additional schematical views of arrangements designed for a method according to the invention.

FIG. 2 schematically shows a first chamber 25 comprising nitrogen and oxygen. By way of example, the first chamber 25 may comprise air which, of course, comprises nitrogen and oxygen. Constituents other than nitrogen and oxygen may be present as well. The nitrogen and oxygen may be held under pressure inside the first chamber 25, for instance under a pressure of 6 bar. In the present example nitrogen and oxygen are obtained from the first chamber 25. On the one hand, nitrogen and oxygen move from the first chamber 25 into the reaction chamber 30. This reaction chamber 30 is similar to the reaction chamber 3 shown in FIG. 1, but does not necessarily comprise, for instance, the isolation 12. In this embodiment, the reaction chamber 30 comprises a heating device 32, in a situation similar to that of the heating device 11 in FIG. 1. Nitrogen and oxygen obtained from the first chamber 25 move into the reaction chamber 30 via the first membrane 2 which reduces the oxygen content of the nitrogen/oxygen mixture. On the other hand, nitrogen and oxygen are obtained from the first chamber 25 via paths 35 and 40 respectively. Membranes 45 and 50 may be used to obtain respectively the nitrogen and oxygen moving along the paths 35 and 40 from the first chamber 25. Similar to the situation shown in FIG. 1, the reaction chamber 30 comprises an optional second membrane 4 for extracting nitric oxide from the reaction chamber 30. Extracted nitric oxide is held in extraction chamber 5. According to the embodiment shown in the present figure, nitrogen obtained from the first chamber 25 is moved along the path 35 and is used as a carrier gas to a transport nitric oxide from the extraction chamber 5 to a location 47 where the nitric oxide is used. Such a location may be a patient who needs the nitric oxide. The nitric oxide together with the nitrogen carrier gas may be put under a pressure exceeding 1 bar for transporting the nitric oxide to the location where it is needed. Oxygen obtained from the first chamber 25 is moved along the path 40 a location where the oxygen is needed. Such a location may again be a patient who needs the oxygen, the same patient as the one who needed the nitric oxide, or some other use. Possible variations on the situation shown in the present figure include the situation in which path 35 is non-existent and the situation in which path 40 is nonexistent. The first chamber 25 need not be in direct contact with the reaction chamber 30 through the first membrane 2. In that case, nitrogen and oxygen need to be provided to the reaction chamber 30 via other means, such as direct feeds. Such situations will be shown in the following figures. Another possible situation is the situation in which the first chamber 25 only comprises nitrogen. Obviously, in this situation path 40 is nonexistent. Still in the latter situation, nitrogen may be provided from the first chamber 25 to the reaction chamber 30 to provide nitrogen for the process gas and/or reducing the relative oxygen content in the process gas. However, nitrogen from the first chamber 25 may also be used exclusively as a carrier gas for extracted nitric oxide in the extraction chamber 5. In all embodiment of the present invention the relative oxygen contend in the process gas in the reaction chamber 30 may be reduced by providing nitrogen to the reaction chamber 30 either from the first chamber 25 or from any other suitable means such as nitrogen storage tanks.

FIG. 3 schematically shows an arrangement similar to the arrangement shown in FIG. 2. The reader is referred to the previous figure for a description of the functioning of the arrangement. Corresponding elements in both figures have been given identical reference numerals. The present figure again shows a first chamber 25, a reaction chamber 30, the heating device 32, paths 35 and 40, an extraction chamber 5, an optional second membrane 4, usage location 47, and membranes 45 and 50. However, in the present figure of the first chamber 25 is not in contact with the reaction chamber 30 via a first membrane 2. Instead, at least part of the nitrogen obtained from the first chamber 25 using membrane 45 and moving along path 35 is siphoned off to flow along the new path 37 to the reaction chamber 30. Similarly, at least part of the oxygen obtained from the first chamber 25 using membrane 50 and moving along path 40 is siphoned off to flow along the new path 42 to the reaction chamber 30. Optional suction pumps 60 and 65 may be used to transport respectively nitrogen and oxygen away from the first chamber 25. Possible variations on the situation shown in the present figure included situation in which path 35 is nonexistent, the situation in which path 37 is nonexistent, the situation in which both paths 35 and 37 are nonexistent, the situation in which path 40 is nonexistent, the situation in which path 42 is nonexistent, and the situation in which both paths 40 and 42 are nonexistent. In situations in which no oxygen is obtained from the first chamber 25, the first chamber 25 obviously does not need to comprise oxygen or a membrane 50 for obtaining oxygen from the first chamber 25. In such situations, oxygen needs to be supplied to the reaction chamber 30 from other means, such as oxygen storage tanks.

FIG. 4 schematically shows a generalization of the concept behind the present invention. A reaction chamber 70 is used to create a gas comprising a target gas needed for a desired purpose. Target gas is extracted from the reaction chamber 70 and held in the extraction chamber 75. For extraction use may be made of the optional membrane 100. The arrangement shown in the present figure further comprises a first chamber 80 comprising an additional gas. At least a first part of the additional gas is obtained from the first chamber 80 and used as a carrier gas for transporting the target gas from the extraction chamber 75 to a location 200 where the target gas is needed. An optional membrane 210 may be used to obtain the first part from the first chamber 80. The first part is transported from the first chamber 80 to the extraction chamber 75 via path 85. Alternatively or additionally, a second part of the additional gas is obtained and transported via path 90 to a further location 200 where the second part is needed. This location may be but need not be the same location as where the target gas needed. A possible location where either the target gas and/or the second part obtained from the additional gas are put to use is a patient in need of the target gas and/or the second part. An optional membrane 220 may be used to obtain the second part from the first chamber 80. As shown in the previous embodiments, the additional gas may comprise nitrogen and oxygen and the first part and the second part of the additional gas may be nitrogen and oxygen respectively. Variations on the situation shown in the present figure include the situation in which path 85 is nonexistent and the situation in which path 90 is nonexistent. Optional suction pumps 105 and 110 may be used to transport the first part and the second part obtained from the first chamber 80 along the paths 85 and 90 respectively. At least a part of the additional gas in the first chamber 80 may be transported into the reaction chamber 70 to support the generation of the gas comprising the target gas. Such transport is not shown in the present figure but is shown in, for instance, the previous two figures. This particular embodiment has the advantage of efficient use of materials available in the arrangement.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. Method for generating nitric oxide comprising the steps of:
   providing a process gas inside a first reaction chamber, wherein the process gas comprises nitrogen gas and oxygen gas;
   heating the process gas to a temperature which is sufficiently high to enable a reaction of oxygen and nitrogen to form nitric oxide, thereby forming a gas which comprises nitric oxide; and
   extracting the nitric oxide comprising gas from the first reaction chamber, wherein the amount of the oxygen gas in the process gas in the first reaction chamber is $\leq 5$ vol-%.

2. Method according to claim 1, wherein at least a portion of the oxygen gas in the first reaction chamber is converted into nitric oxide.

3. Method according to claim 1, further comprising treating air to generate the process gas.

4. Method according to claim 1, wherein the oxygen is present in the process gas in the first reaction chamber with a partial pressure of 20 Pa.

5. Method according to claim 1, wherein nitric oxide is present in the generated nitric oxide comprising gas in an amount of $\geq 10$ ppm-$\leq 1000$ ppm.

6. Method according to claim 1, wherein the process gas is heated to a temperature range of $\geq 1000$K.

7. Method according to claim 1, wherein the first reaction chamber is isolated by a heat isolation.

8. Method according to claim 1, wherein the oxygen content in the first reaction chamber is achieved by guiding the process gas through a first membrane.

9. Method according to claim 1, wherein the generated nitric oxide comprising gas is extracted from the first reaction chamber into an extraction chamber through a second membrane.

10. Method according to claim 1, further comprising providing a cooling phase following the heating step.

11. Method according to claim 10, further comprising providing the process gas to a second reaction chamber: wherein heating the process gas in the first reaction chamber takes place while the second reaction chamber is in a cooling phase, and wherein heating the process gas in the second reaction chamber takes place while the first reaction chamber is in a cool phase.

12. Method according to claim 1, wherein the method comprises the following additional steps:
   providing a second reaction chamber;
   obtaining nitrogen gas from an additional gas treated in the second reaction chamber;
   using the obtained nitrogen gas as a carrier gas for transporting nitric oxide extracted from the first reaction chamber and/or guiding the obtained nitrogen gas into the first reaction chamber.

13. Method according to claim 12, wherein the additional gas further comprises oxygen, and the method further comprises:
   obtaining oxygen gas from the additional gas;
   guiding at least part of the obtained oxygen gas into the first reaction chamber.

* * * * *